(12) United States Patent
Takahashi et al.

(10) Patent No.: US 6,670,627 B2
(45) Date of Patent: Dec. 30, 2003

(54) APPARATUS AND METHOD FOR CONTINUOUS SURFACE EXAMINATION COMPRISING A LIGHT SHIELDING MEMBER AT OUTER ENDS OF THE EXAMINED SURFACE

(75) Inventors: Ippei Takahashi, Kanagawa (JP); Hiroshi Tsuzaki, Shizuoka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/120,788

(22) Filed: Apr. 12, 2002

(65) Prior Publication Data

US 2002/0148985 A1 Oct. 17, 2002

(30) Foreign Application Priority Data

Apr. 13, 2001 (JP) ........................................ 2001-115755

(51) Int. Cl.$^7$ .................................................. G01V 8/00
(52) U.S. Cl. ............................ 250/559.42; 250/559.48; 356/238.2; 356/431
(58) Field of Search ................................ 250/235, 236, 250/559.48, 559.42, 559.45; 356/239.1, 239.7, 238.2, 429, 430, 431

(56) References Cited

U.S. PATENT DOCUMENTS 3,980,891 A * 9/1976 Slaker ................... 250/559.06
4,401,893 A * 8/1983 Dehuysser ............. 250/559.49
5,166,535 A * 11/1992 Takahashi ............... 250/559.24
5,969,373 A * 10/1999 Harris .................... 250/559.42

FOREIGN PATENT DOCUMENTS

| JP | 63-115746 | | 7/1988 | |
| JP | 4-125455 | | 4/1992 | |
| JP | 04125455 A | * | 4/1992 | .......... G01N/21/89 |
| JP | 8-247963 A | | 9/1996 | |
| JP | 3380321 B2 | | 12/2002 | |

* cited by examiner

Primary Examiner—Stephone Allen
Assistant Examiner—Christopher W. Glass
(74) Attorney, Agent, or Firm—Sughrue Mion, PLLC

(57) ABSTRACT

A surface examining apparatus irradiates an examinatorial light from a projector on a examined body that runs in a Z-direction. The projector is arranged at a distance from the surface of the examined body in a Y-direction orthogonal to the surface thereof and arranged inwardly of outer ends of the examined body in the width direction thereof in the X-direction orthogonal to the Z-direction and the Y-direction, and which detects the light that has passed through the examined body thereby to examine surface defects of the examined body. A light shielding unit is provided, which includes a light shielding member arranged between the projector and the examined body and shields the examinatorial light that is going to travel outwards from the outer end in the width direction of the examined body, and a moving unit that moves the light shielding member in the X-direction and in the Y-direction.

23 Claims, 5 Drawing Sheets

APPARATUS AND METHOD FOR CONTINUOUS SURFACE EXAMINATION COMPRISING A LIGHT SHIELDING MEMBER AT OUTER ENDS OF THE EXAMINED SURFACE

BACKGROND OF THE INVENTION

The present invention relates to a technology for examining surface defects of a belt-like body to be examined such as a web, that runs continuously.

In order to examine surface defects of a plastic film, a sheet, a thin metal foil, their laminated sheets, or another belt-like body, there are various surface examining apparatuses.

As one of them, there is a surface examining apparatus which irradiates an examinatorial light the surface of a body to be examined (herein after, referred to as "an examined body") to detect its permitted light or its reflected ii ht by a light receiver and detects photoelectrons. Then, the surface examining apparatus detects the presence of the surface defects by this photoelectric detection outputted. In the surface examining apparatus, a light shielding plate is used in order to prevent the examinatorial light incident directly on the light receiver in error.

Various modes of the light shielding plate are disclosed in JP-UM-A-63-115746. Herein, a light shielding plate is arranged between a projector and an examined body. The examined body is irradiated with a laser beam used as an examinatorial light in such a manner that the laser beam traverses in a width direction of the examined body. The laser beam that is going to travel outward from outer ends in the width direction of the examined body (referred to also as "edges") is shielded by the light shielding plate. Thus, the laser beam traveling outward from the edges of the examined body is prevented from being incident directly on a light receiver.

In JP-A-04-125455, a surface examining apparatus is disclosed, which can allow a light shielding plate to follow the movement of the edge of an examined body, when the examined body meanders. The examined body is irradiated with a laser beam in the shape of a circular arc (a quarter sector) centered on a projector. A rotary member that comes into contact with the edge of the examined body is coupled to the light shielding plate arranged between the projector and the examined body. While the edge of the examined body does not move in a width direction thereof and the examined body runs normally, the rotary member only rotates and does not move in the width direction. However, when the edge moves in the width direction with meandering of the examined body, the rotary member is moved in the width direction, so that the light shielding plate coupled to the rotary member is also moved in the width direction. According to this technology, the surface examining apparatus can correspond to not only meandering of the examined body but also change in width dimension of the examined body, so that the laser beam that is going to be incident directly on a light receiver can be shielded by the light shielding plate.

In the surface examining apparatus disclosed in the JP-A-04-125455, when the edge of the examined body moved in the width direction, the light shielding plate had a tendency of larger movement than that is desired in the width direction. The edge of the examined body is irradiated slantingly with the laser beam traveling toward the examined body in the shape of the circular arc (a quarter sector) centered on the projector. Generally, the normal running state where the edge of the examined body is not moving in the width direction is assumed, and the position in the width direction of the light shielding plate placed between the projector and the examined body is set so that the edge of the examined body can be irradiated with the laser beam and so that the laser beam traveling outward of the edge can be completely shielded by the light shielding plate.

For example, when the edge moves closer to the center of the examined body than the position in the normal running state with meandering of the examined body (i.e., the width of the examined body along line $50a$ decreases), the light shielding plate is also moved inward by the same distance. At this time, the laser be is excessively shielded by the light shielding plate, so that the edge of the examined body is not irradiated. Since the light shielding plate is closer to the projector side than the examined body side and the edge of the examined body is irradiated slantingly with the laser beam, in case that the light shielding plate is moved by the same distance as the distance by which the edge has moved, the light shielding plate shields the laser beam excessively. Therefore, the surface examination cannot be performed with a high accuracy.

SUMMARY OF THE INVENTION

The present invention has been made in view of the above circumstances, and its object is to provide a surface examining apparatus and a surface examining method in which the light shielding plate can be suitably moved in accordance with the movement of the edge of the examined body.

The object of the invention is achieved by a first aspect of the present invention, there is provided a surface examining apparatus for examining surface defects of a belt-like examined body comprising: a projector irradiating an examinatorial light on the examined body that runs continuously in a Z-direction, and arranged at a distance from a surface of the examined body in a Y-direction orthogonal to the surface of the examined body and arranged inwardly of outer ends of the examined body in the width direction thereof in an X-direction orthogonal to both of the Z-direction and the Y-direction; a light receiver detecting the light that has passed through the examined body; and a light shielding unit including a light shielding member that is arranged between the projector and the examined body and shields the examinatorial light that is going to travel outwards from the outer ends of the examined body in the width direction thereof, and a moving unit that moves the light shielding member in the X-direction and in the Y-direction.

Further, the object of the invention is achieved by a second aspect of the present invention, in which there is provided a surface examining method for examining surface defects of a belt-like examined body comprising steps of: preparing the examined body that runs continuously in a Z-direction; preparing a projector arranged at a distance from the surface of the examined body in a Y-direction orthogonal to the surface of the examined body and arranged inwardly of the outer ends of the examined body in the width direction thereof in an X-direction orthogonal to both of the Z-direction and the Y-direction; preparing a light shielding member arranged between the projector and the examined body; irradiating an examinatorial light from the projector on the examined body; moving the light shielding member in the X-direction and in the Y-direction according to the positional change of the outer end of the examined body in the width direction thereof, thereby to shield the examinatorial light that is going to travel outwards from the outer ends in the width direction of the examined body; and detecting the light that has passed through the examined body by a light receiver.

According to the above structures, the light shielding member can be moved not only in the X-direction which is a direction along the width direction of the examined body but also in the Y-direction which is a direction toward the projector from the examined body. Hereby, the light shielding member can be accurately moved in accordance with the positional change of the edge of the examined body. Therefore, by the light shielding member, the edge is always permitted to be irradiated with the examinatorial light and the examinatorial light traveling outward of the edge can be surely shielded.

In the above constitution, it is preferable that the surface examining apparatus as set forth in the first aspect of the present invention, further comprising a sensor for detecting the position of the outer end of the examined body in the width direction thereof, wherein the moving unit moves the light shielding member on the basis of the state of the sensor.

Further, in the above structure, it is preferable that the moving unit moves a leading end of the light shielding member nearly along a curve drawn by an expression [1], $$y = d \times L / (d - x) \quad [1]$$

in which y represents a position in the Y-direction of the leading end of the light shielding member, x represents a position in the X-direction of the leading end of the light shielding member, d represents a distance in the X-direction from the origin to the projector, L represents a distance in the Y-direction from the origin to the leading end of the light shielding member, and the origin of the expression [1] is a position of the outer end of the examined body in the width direction thereof in the normal running state. Further the moving unit moves the leading end of the light shielding member along an approximate straight line or an approximate curve of the curve drawn by the expression [1].

Further, in the above structure, it is preferable that the moving unit further includes a guide having a shape nearly according to the curve drawn by the expression [1], and the light shielding member is moved along the guide.

DESCRIPTION OF THE PREDERRED EMBODIMENT

One embodiment of the present invention will be described below with reference to drawings.

Figure 1:
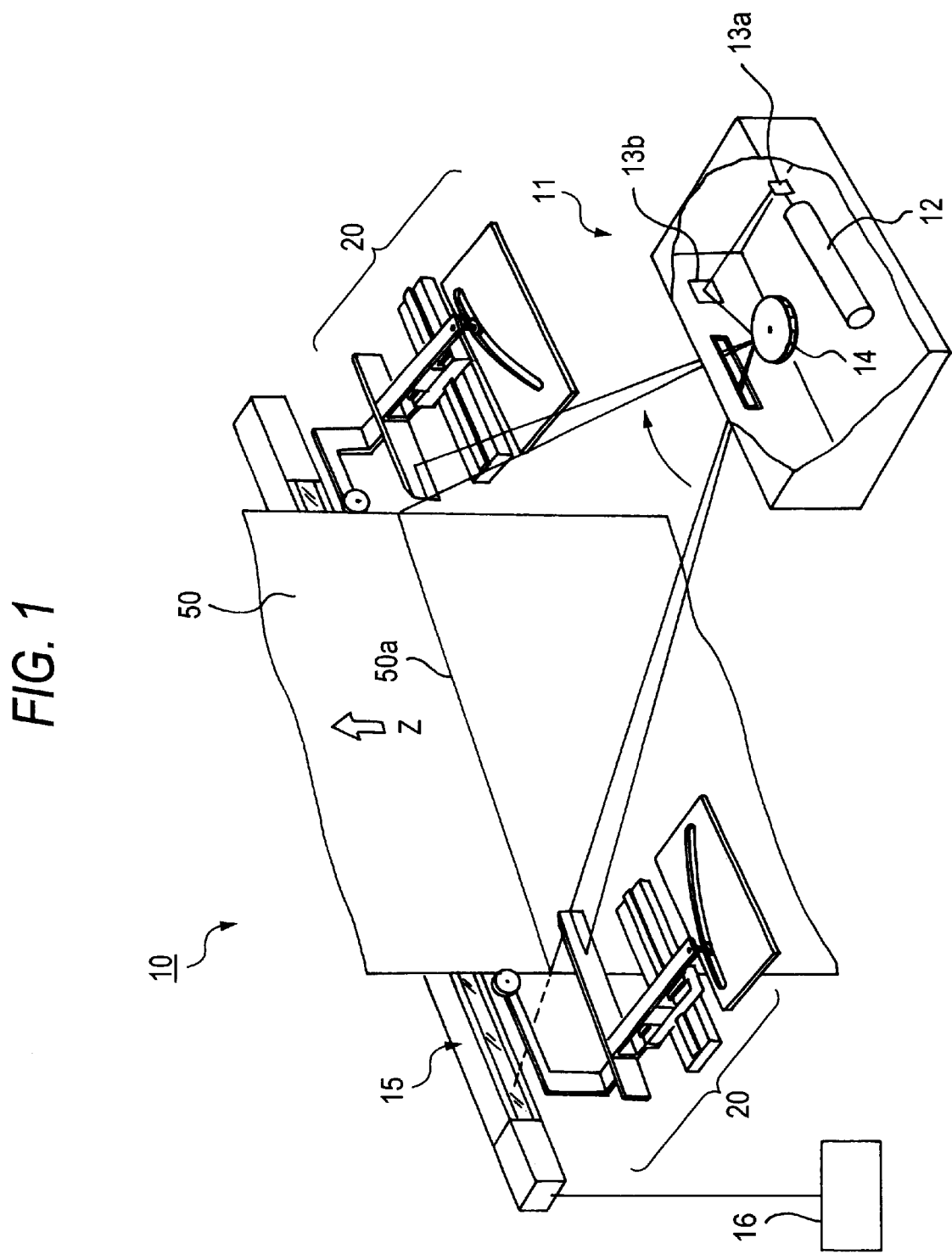
FIG. 1 is a schematic perspective view showing one embodiment of the present invention.

FIG. 1 is a schematic perspective view of a surface examining apparatus 10 that is one embodiment of the present invention. The surface examining apparatus 10 runs a web 50 that is a belt-like examined body between a projector 11 and a light receiver 15.

The projector 11 comprises a laser beam source 12, reflective mirrors 13a, 13b, and a rotary mirror 14 functioning as a scanning unit, which are housed in a housing. The web 50 is irradiated with the laser beam from the projector 11 in the shape of a circular arc centered on the rotary mirror 14. The laser beam is applied onto a line 50a that traverses the web 50 in the width direction. For example, the laser beam scans on the surface of the web 50 from a left edge of the web 50 to a right edge thereof. The laser beam is incident on the surface of the web 50 nearly perpendicular.

For example, in case that there is a coating defect in the web 50, the web 50 transmits light at its defect position, and its light (the light that has passed through the web 50) is incident on the light receiver 15. The light that has been incident on the light receiver 15 is appropriately converted into an electrical signal (photoelectrically converted), and its electrical signal is sent to a signal processor 16, whereby the existence of the defect is recognized.

While the laser beam is applied on the line 50a of the web 50 from the left edge to the right edge, the web 50 is transported in the Z-direction shown in FIG. 1, whereby the entire surface of the web 50 is examined.

Near both ends in the width direction of the web 50, the light shielding units 20 are respectively provided.

Figure 2:
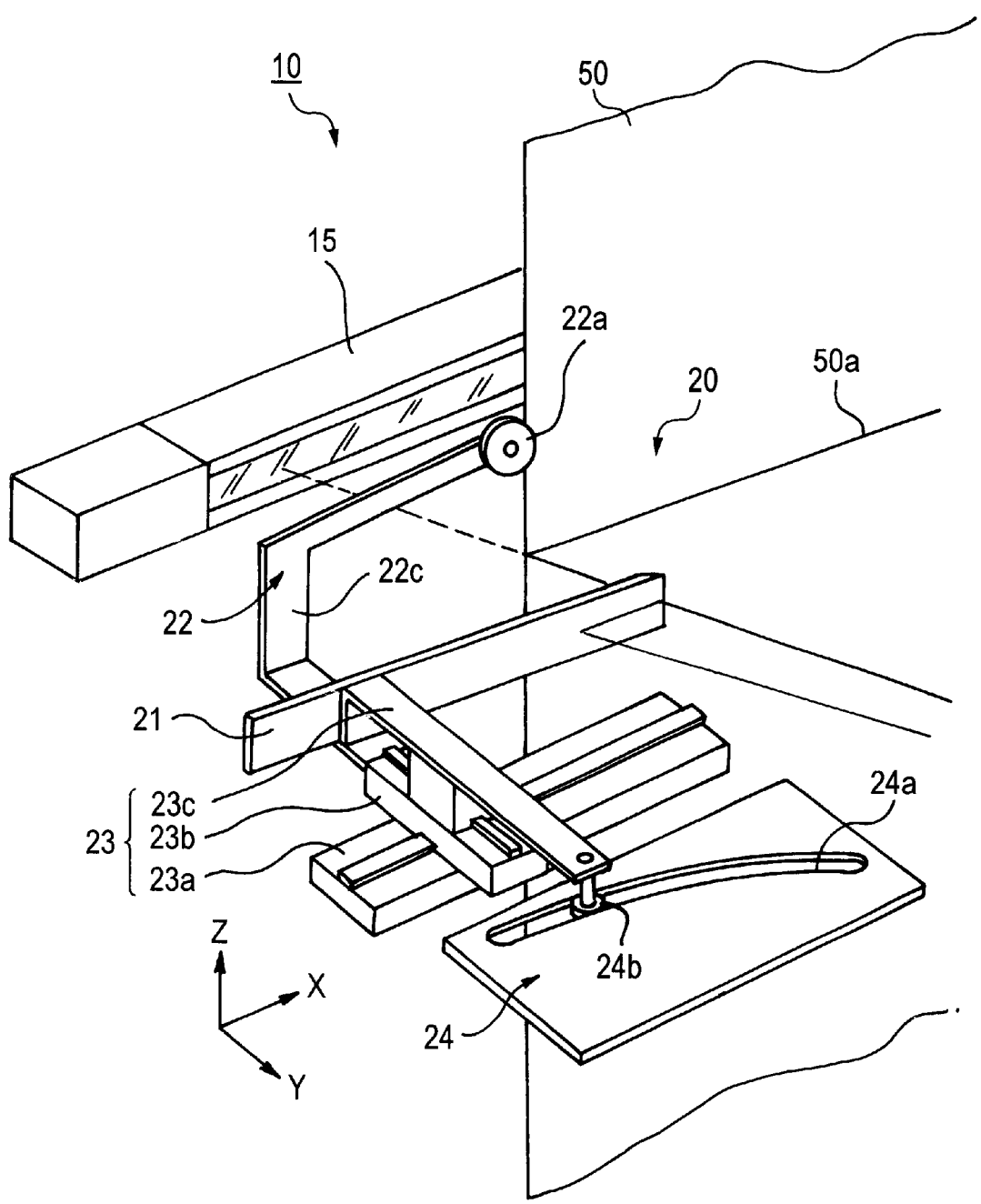
FIG. 2 is a main portion enlarged view of a surface examining apparatus of FIG. 1.

FIG. 2 is an enlarged view of one of the light shielding units 20. The light shielding unit 20 comprises a light shielding plate 21 arranged between the web 50 and the projector 11 shown in FIG. 1, an edge sensor 22 which detects an edge position of the web 50, and a moving unit 23 which moves the light shielding plate 21.

As the light shielding plate 21, a rectangular plate member is used here. The longitudinal direction of the light shielding plate 21 is parallel to the width direction (X-direction) of the web 50. The position of the leading end (end on the center side in the width direction of the web 50) of the light shielding plate 21, viewed in the X-direction, protrudes toward the center side in the width direction of the web 50 rather than the edge position of the web 50. The position of the leading end of the light shielding plate 21, viewed in the Z-direction, is equal to the positions of the line 50a and the light receiver 15.

The edge sensor 22 comprises a pulley 22a functioning as a rotary member that comes rotatably into contact with the edge of the web 50, and a first coupling piece 22c that couples the pulley 22a and the light shielding plate 21. The pulley 22a, viewed in the Y-direction orthogonal to the Z-direction and the X-direction, is nearer to the light receiver 15 than to the light shielding plate 21. Namely, the first coupling piece 22c couples the pulley 22a and the light shielding plate 21 which are offset in the Y-direction.

To the light shielding plate 21, a second coupling piece 23c extending from the light shielding plate 21 to the projector side, viewed in the Y-direction is connected. The second coupling piece 23c couples the light shielding plate 21, and an X-moving section 23a and a Y-moving section 23b of the moving unit 23.

In this embodiment, the second coupling piece 23c is moved on a rail of the Y-moving section 23b in the Y-direction. And, the Y-moving section 23b is moved on a rail of the X-moving section 23a in the X-direction. The X-moving section 23a is fixed, and the Y-moving section 23b is moved on the rail of the X-moving section 23a together with the second coupling piece 23c in the X-direction. The second coupling piece 23c, by a guide member 24 which will be described later, is moved on the rail of the Y-moving section 23b also in the Y-direction when it is moved in the X-direction.

For the leading end (end on the projector side) of the second coupling piece 23c, a pin extending up and down (in the Z-direction) is provided. For the leading end of its pin, a rotary disc 24b that is a guided member is provided. The rotary disc 24b is rotatably fitted into a curve-shaped guide groove 24a formed in a flat plate guide member 24.

How to determine the curve shape of the guide groove 24a will be described below.

Figure 3:
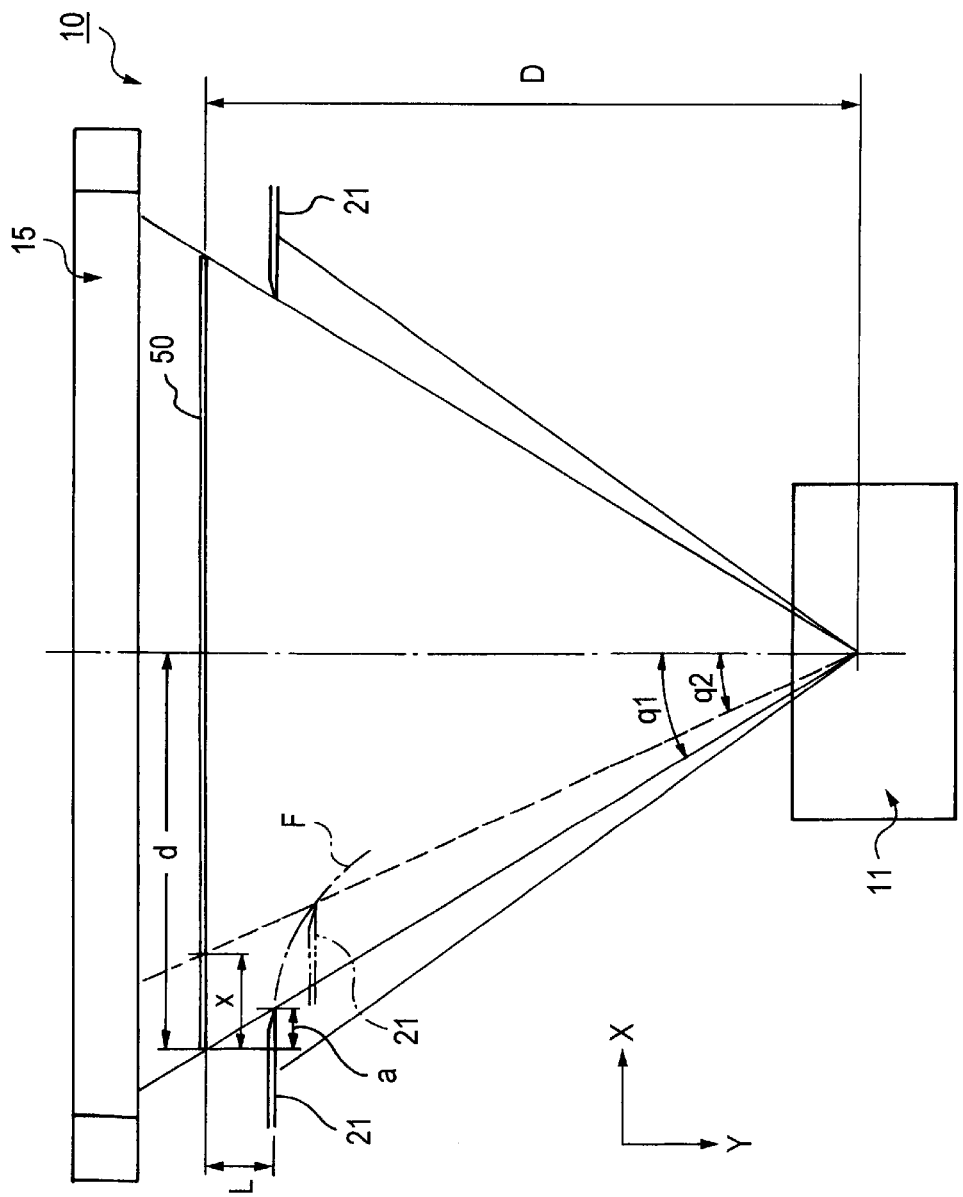
FIG. 3 is a top view of the surface examining apparatus of FIG. 1.

FIG. 3 is a schematic top view (X-Y plan view) of the surface examining apparatus 10, viewed in the Z-direction. Viewed in the X-direction, a center position of the web 50 is equal to a center position of the projector 11. A reference character d represents a distance (half width) from the center of the web 50 to the edge. Further, a reference character D represents a distance from the web 50 to the projector 11, viewed in the Y-direction.

An initial position of the light shielding plate 21 is drawn with a solid line. A state of the plate 21 when the edge position of the web 50 varies is drawn with a chain double-dashed line.

The initial position of the light shielding plate 21 is set on the assumption of the edge position of the web 50 in the normal running state. Namely, the initial position of the light shielding plate 21 is set so that the edge of the web 50 in the normal running state can be irradiated with the laser beam from the projector 11. In addition, the initial position of the light shielding plate 21 is also set so that the laser beam that is going to travel outward of the edge is completely shielded by the light shielding plate 21. Under this state, a distance between the leading end of the light shielding plate 21 and the edge of the web 50, viewed in the X-direction is represented by a reference character a, and a distance between the leading end of the light shielding plate 21 and the edge of the web 50, viewed in the Y-direction is represented by a reference character L. Further, an angle formed by the leading end of the light shielding plate 21 under this state, the projector 11 and the center in the width direction of the web 50 is represented by a reference character $\theta_1$. Namely, in the normal running state, a center angle (scanning angle) of the laser beam applied toward the web 50 in the shape of the circular arc is represented by $2 \times \theta_1$.

In case that the edge position of the web 50 has moved more to the inside due to meandering of the web 50 than in the normal running state, the light shielding plate 21 is moved to the position shown by the chain double-dashed line. At this time, the leading end of the light shielding plate 21 is moved along a curve F shown by a chain line in FIG. 3.

An angle formed, when the edge position of the web 50 has moved more to the inside than in the normal running state, by the leading end of the light shielding plate 21, the projector 11 and the center in the width direction of the web 50 is represented by a reference character $\theta_2$.

Figure 4:
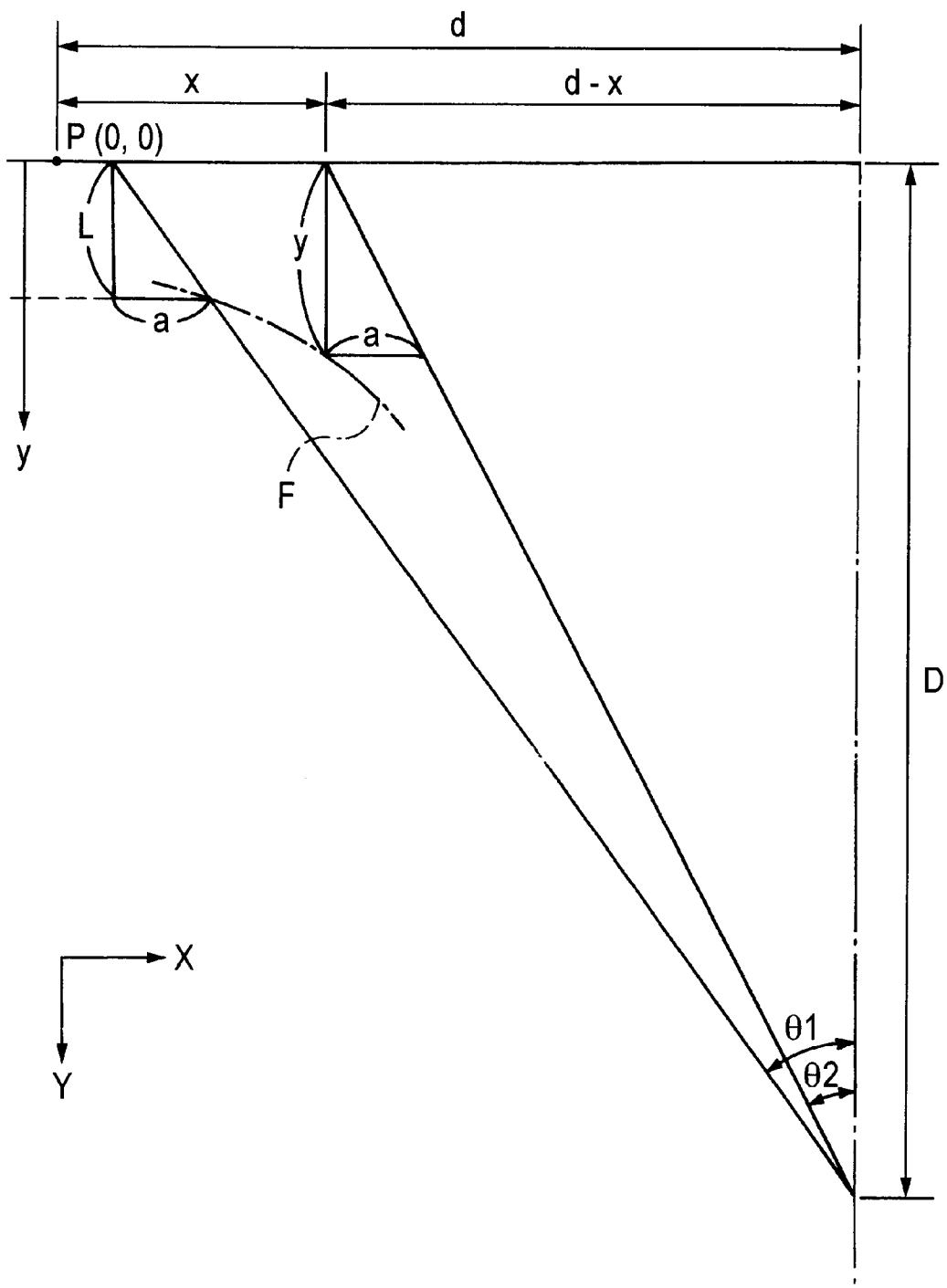
FIG. 4 is a diagram in which the positional relation among members is shown geometrically.

The positional relation among the above-described members is geometrically shown in FIG. 4. Hereinafter, the edge position of the web in the normal running time is taken as the origin P on the X-Y plane surface.

As clear from FIG. 4, $\tan(\theta_1) = d/D$. Since $d/D = a/L$, $a = d \times L/D$.

Further, as known from FIG. 4, $\tan(\theta_2) = (d-x)/D$. Since $(d-x)/D = a/y$, $y = D \times a/(d-x)$.

From the above expressions, the following expression is obtained: $y = d \times L/(d-x)$. This expression becomes an expression of the curve F.

This curve F can be taken as the curve shape of the guide groove 24a shown in FIG. 2, viewed from the top surface.

Figure 5:
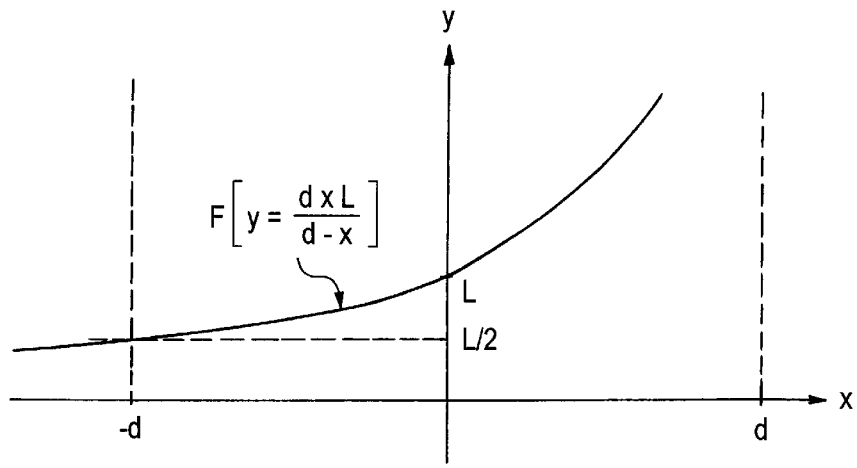
FIG. 5 is a diagram for explaining a curve F of a guide member.

This curve F $[y = d \times L/(d-x)]$, as shown in FIG. 5, is a curve having $\{x=d, y=0\}$ as an asymptotic line.

Figure 6:
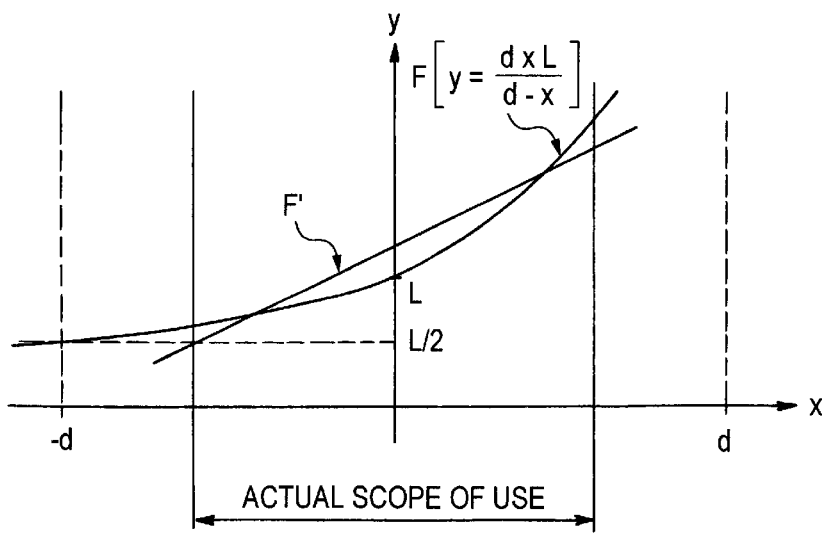
FIG. 6 is a diagram for explaining an approximate straight line F'.

As shown in FIG. 6, instead of the curve shape of the guide groove 24a shown in FIG. 2, an approximate straight line F' of the curve F is found, and this line F' may be used as the shape of the guide groove 24a. Namely, the line F' may be used in place of the curve F as long as a really used range where this approximate straight line F' overlaps nearly with the curve F is a really used range. Hereby, the guide member 24 is readily manufactured, so that cost performance can be improved.

The present invention is not limited to the before-mentioned embodiment but appropriate modifications and improvements are possible.

For example, using a curve approximate to the curve F in place of the approximate straight line F' shown in FIG. 6, the guide groove of the guide member may be formed. Further, along a line approximate to the curve F, the light shielding member may be moved using plural straight lines.

For example, instead of the X-moving section 23a and the Y-moving section 23b, a moving section having a rail along the curve F or the approximate straight line F' may be provided. Namely, using a single mechanism, the light shielding member may be constituted so as to move two-dimensionally or three-dimensionally.

For example, a surface of the light shielding plate 21, opposed to the web 50 may be a surface of inclination that inclines in relation to the web 50 surface.

Further, as the edge sensor, in addition to a contact type having the pulley, a non-contact type having a photoelectric sensor or an airflow sensor may be used.

The technical idea of the present invention can be applied also to surface examination of a type which examines a reflective light from a examined body by a light receiver.

As described above, according to the present invention, it is possible to provide a surface examining apparatus and a surface examining method in which a light shielding plate can be suitably moved in accordance with the movement of edge of a examined body, so that surface examination having high accuracy can be executed.

What is claimed is:

1. A surface examining apparatus for examining surface defects of a belt-like examined body comprising:

a projector irradiating an examinatorial light on the examined body that runs continuously in a Z-direction, and arranged at a distance from a surface of the examined body in a Y-direction orthogonal to the surface of the examined body and arranged inwardly of outer ends of the examined body in the width direction thereof in an X-direction orthogonal to both of the Z-direction and the Y-direction;

a light receiver detecting the light that has passed through the examined body; and a light shielding unit including a light shielding member that is arranged between the projector and the examined body and shields the examinatorial light that is going to travel outwards from the outer ends of the examined body in the width direction thereof, and a moving unit that moves the light shielding member in the X-direction and in the Y-direction simultaneously.

2. The surface examining apparatus as set forth in claim 1, further comprising a sensor for detecting the position of the outer end of the examined body in the width direction thereof, wherein the moving unit moves the light shielding member on the basis of the state of the sensor.

3. The surface examining apparatus as set forth in claim 1, wherein the moving unit moves a leading end of the light shielding member nearly along a curve drawn by $$y = d \times L/(d-x)$$

in which y represents a position in the Y-direction of the leading end of the light shielding member, x represents a position in the X-direction of the leading end of the light shielding member, d represents a distance in the X-direction from an origin to the projector, L represents a distance in the Y-direction from the origin to the leading end of the light shielding member, and the origin is a position of the outer end of the examined body in the width direction thereof in the normal running state.

4. The surface examining apparatus as set forth in claim 2, wherein the moving unit moves a leading end of the light shielding member nearly along a curve drawn by $$y = d \times L/(d-x)$$

in which y represents a position in the Y-direction of the leading end of the light shielding member, x represents a position in the X-direction of the leading end of the light shielding member, d represents a distance in the X-direction from an origin to the projector, L represents a distance in the Y-direction from the origin to the leading end of the light shielding member, and the origin is a position of the outer end of the examined body in the width direction thereof in the normal running state.

5. The surface examining apparatus as set forth in claim 3, wherein the moving unit further includes a guide having shape nearly according to the curve drawn by $y = d \times L/(d-x)$, and the light shielding member is moved along the guide.

6. The surface examining apparatus as set forth in claim 4, wherein the moving unit further includes a guide having shape nearly according to the curve drawn by $y = d \times L/(d-x)$, and the light shielding member is moved along the guide.

7. The surface examining apparatus as set forth in claim 1, wherein the moving unit further includes a guide having a shape that approximates a straight line, and the light shielding member is moved along the guide.

8. The surface examining apparatus as set forth in claim 2, wherein the moving unit further includes a guide having a shape that approximates a straight line, and the light shielding member is moved along the guide.

9. A surface examining method for examining surface defects of a belt-like examined body, wherein the method comprises:
   preparing the examined body that runs continuously in a Z-direction;
   preparing a projector arranged at a distance from the surface of the examined body in a Y-direction orthogonal to the surface of the examined body and arranged inwardly outer ends of the examined body in the width direction thereof in an X-direction orthogonal to both of the Z-direction and the Y-direction;
   preparing a light shielding member arranged between the projector and the examined body;
   irradiating an examinatorial light from the projector on the examined body;
   moving the light shielding member in the X-direction and in the Y-direction simultaneously according to the positional change of the outer end of the examined body in the width direction thereof, thereby to shield the examinatorial light that is going to travel outwards from the outer ends in the width direction of the examined body; and
   detecting light that has passed through the examined body by a light receiver.

10. The surface examining method as set forth in claim 9, wherein the method further comprises detecting a position of the outer end of the examined body in the width direction thereof by a sensor so that the light shielding member is moved on the basis of the state of the sensor.

11. The surface examining method as set forth in claim 9, wherein a leading end of the light shielding member is moved nearly along a curve drawn by $$y = d \times L/(d-x)$$

in which y represents a position in the Y-direction of the leading end of the light shielding member, x represents a position in the X-direction of the leading end of the light shielding member, d represents a distance in the X-direction from an origin to the projector, L represents a distance in the Y-direction from the origin to the leading end of the light shielding member, and the origin is a position of the outer end of the examined body in the width direction thereof in the normal running state.

12. The surface examining method as set forth in claim 9, wherein the light shielding member is moved along a guide having a shape approximating a straight line.

13. The surface examining apparatus as set forth in claim 11, wherein the light shielding member is moved along a guide having a shape nearly according to the curve drawn by $y = d \times L/(d-x)$.

14. A surface examining apparatus for examining surface defects of a belt-like examined body that runs continuously in a first direction, the apparatus comprising:
   a projector irradiating an examinatorial light on the examined body, and arranged at a distance from a surface of the examined body and arranged between outer ends of the examined body in the width direction thereof;
   a light receiver detecting examinatorial light that has passed through the examined body; and
   a light shielding unit comprising:
      a light shielding member arranged between the projector and the examined body and preventing examinatorial light from traveling beyond the outer ends of the examined body in the width direction thereof, and
      a moving unit that moves the light shielding member in a second direction parallel to a width direction across the examined body while concurrently moving the light shielding member in a third direction that is orthogonal to the examined body.

15. The surface examining apparatus as set forth in claim 14, further comprising a sensor for detecting the position of the outer end of the examined body in the width direction thereof, wherein the moving unit moves the light shielding member on the basis of the state of the sensor.

16. The surface examining apparatus as set forth in claim 14, wherein the moving unit moves a leading end of the light member nearly along a curve drawn by $$y = d \times L/(d-x)$$

in which y represents a distance of the leading end of the light shielding member from the surface of the examined body in the third direction, x represents a distance of the leading end of the light shielding member from an origin in the second direction, d represents a distance in the third direction from the origin to the projector, L represents an initial distance in the third direction from the origin to the leading end of the light shielding member, and the origin is a position of the outer end of the examined body in the width direction thereof in the normal running state.

17. The surface examining apparatus as set forth in claim 16, wherein the moving unit further comprises a guide having a shape nearly according to the curve drawn by $$y = d \times L/(d-x),$$

and the light shielding member is moved along the guide.

18. The surface examining apparatus as set forth in claim 14, wherein the moving unit further comprises a guide having a shape that approximates a straight line, and the light shielding member is moved along the guide.

19. A surface examining method for examining surface defects of a belt-like examined body that runs continuously in a first direction, wherein the method comprises:

preparing a projector arranged at a distance from the surface of the examined body and arranged between outer ends of the examined body in the width direction thereof;

preparing a light shielding member arranged between the projector and the examined body;

irradiating examinatorial light from the projector on the examined body;

moving the light shielding member concurrently in a second direction parallel to a width direction across the examined body and in a third direction orthogonal to the examined body according to the positional change of the outer end of the examined body in the width direction thereof, thereby preventing examinatorial light from traveling outwards from the outer ends in the width direction of the examined body; and detecting examinatorial light that has passed through the examined body by a light receiver.

20. The surface examining method as set forth in claim 19, wherein the method further comprises detecting a position of the outer end of the examined body in the width direction thereof by a sensor so that the light shielding member is moved on the basis of the state of the sensor.

21. The surface examining method as set forth in claim 19, wherein a leading end of the light shielding member is moved nearly along a curve drawn by $$y = d \times L/(d-x)$$

in which y represents a position in e Y-direction of the leading end of the light shielding member, x represents a position in the X-direction of the leading end of the light shielding member, d represents a distance in the X-direction from an origin to the projector, L represents a distance in the Y-direction from the origin to the leading end of the light shielding member, and the origin is a position of the outer end of the examined body in the width direction thereof in the normal running state.

22. The surface examining method as set forth in claim 19, wherein the light shielding member is moved along a guide having a shape approximating straight line.

23. The surface examining apparatus as set forth in claim 21, wherein the light shielding member is moved along a guide having a shape nearly according to the curve drawn by $$y = d \times L/(d-x).$$

* * * * *